(12) United States Patent
Ohmori et al.

(10) Patent No.: US 7,790,209 B2
(45) Date of Patent: Sep. 7, 2010

(54) TOTAL ENTERAL NUTRITIOUS COMPOSITION

(75) Inventors: Toshihiro Ohmori, Shizuoka (JP); Naoki Hayashi, Shizuoka (JP); Kiyoshi Fujita, Tokyo (JP); Hideki Tanaka, Tokyo (JP); Kazunori Saima, Shizuoka (JP); Itaru Kon, Shizuoka (JP); Miki Tomoe, Fukuoka (JP)

(73) Assignee: Ajinomoto Co., Inc., Tokyo (JP)

( * ) Notice: Subject to any disclaimer, the term of this patent is extended or adjusted under 35 U.S.C. 154(b) by 595 days.

(21) Appl. No.: 11/689,744

(22) Filed: Mar. 22, 2007

(65) Prior Publication Data

US 2007/0212448 A1 Sep. 13, 2007

Related U.S. Application Data

(63) Continuation of application No. PCT/JP2005/017379, filed on Sep. 21, 2005.

(30) Foreign Application Priority Data

Sep. 22, 2004 (JP) ............................. 2004-275527
Dec. 1, 2004 (JP) ............................. 2004-348106

(51) Int. Cl.
*A61K 38/01* (2006.01)
*A61K 38/00* (2006.01)

(52) U.S. Cl. ............................. 426/72; 514/2; 514/21; 514/23; 424/655; 424/442; 424/600; 426/800; 426/801; 426/658

(58) Field of Classification Search ................... None
See application file for complete search history.

(56) References Cited

U.S. PATENT DOCUMENTS

| 5,438,042 | A  | * | 8/1995 | Schmidl et al. | ............... | 514/21 |
| 6,194,379 | B1 | * | 2/2001 | McEwen et al. | ............... | 514/2 |
| 6,200,950 | B1 | * | 3/2001 | Mark et al. | ............... | 514/2 |

FOREIGN PATENT DOCUMENTS

| JP | 4-51872 | 2/1992 |
| JP | 4-152861 | 5/1992 |
| JP | 5-236909 | 9/1993 |
| JP | 3102645 | 8/2000 |
| JP | 2001-316278 | 11/2001 |
| JP | 2002-119250 | 4/2002 |
| JP | 2004-41006 | 2/2004 |
| JP | 2004-51494 | 2/2004 |

OTHER PUBLICATIONS

Kiyoshi Wakugami, et al., "Biryo Genso Kyoka Ryudoshoku no Mondaiten to keicho Eiyo Kanri ni Okeru Jokuso Yobo no Tameno Aen Hoku Koka no Kufu.", Journal of Japanese Society of Chemical Nutrition, vol. 24, No. 4, XP-002996346, 2003, pp. 255-260 (with English translation).

Kiyoshi Wakugami, et al, "Biryo Genso no Igi.", JJPEN, vol. 25, No. 1, XP-002996347, 2003, pp. 13-20 (with English translation).

Ken Shikoshi, et al., "Jokuso to Eiyo Kensa-Biryo Genso no Juyosei mo Fukumete-", Rinsho Byori Review Tokushu, No. 127, XP-002996348, 2003, pp. 92-98.

Yoichi Koshibu, et al., "Ekijo Koeiyo Ryudoshoku CZ-F no Shiyo Seiseki-Choki Keicho Eiyo Shiko Kanja o Taisho to Shite-" JJPEN., vol. 22, No. 7, XP-002997930, 2000, pp. 487-501, (with English translation).

Yasushi Miyazawa, et al., "No Shinkei Geka Ryoiki ni Okeru Okunos NT-3 no Shiyo Keiken.", JJPEN, XP002997931, vol. 19, No. 11, 1997, pp. 1099-1105 (with English translation).

Kazumi Uechi, et al., "2. Questionnairing to patients under enteral nutrition in Okinawa Prefecture-Changes in actual conditions before and after the enforcement of care insurance-" Intravenous Enteral Alimentation, vol. 17, No. 1, 2002, pp. 82, (with English translation).

(Continued)

*Primary Examiner*—Jennifer C McNeil
*Assistant Examiner*—Hong Mehta
(74) *Attorney, Agent, or Firm*—Oblon, Spivak, McClelland, Maier & Neustadt, L.L.P.

(57) ABSTRACT

The invention provides a total enteral nutritious composition containing proteins, sugars, fats, minerals and vitamins, which improves serum albumin and ameliorates bedsores. The total enteral nutritious composition has a zinc/copper weight ratio of 10-25, and a zinc content of 1.5 mg or greater, a copper content of 0.075-0.15 mg, a sodium content of at least 185 mg, a vitamin B1 content of at least 0.30 mg, a vitamin B2 content of at least 0.25 mg and a protein content of at least 4.0 g, per 100 kcal of the composition. Preferably it has a protein content of at least 5.0 g, a vitamin B6 content of at least 0.30 mg, a biotin content of at least 1.0 μg, a vitamin B12 content of at least 0.20 μg, a folic acid content of at least 20 μg, a β-carotene content of at least 100 μg and a vitamin C content of at least 10 mg. Medium-chain fatty acid oils preferably constitute 35% by weight of the fats of the fat source, per 100 kcal of the composition. The preferred composition viscosity is 6-18 mPa·s (25° C.)

18 Claims, No Drawings

OTHER PUBLICATIONS

Kiyoshi Wakugami, et al., "14. Actual Conditions of enteral nutrition from safety management of trace elements in patients under enteral nutrition", Intravenous Enteral Alimentation, vol. 17, No. 1, p. 90, 2002, (with English translation).

Naoko Matuda, et al., "17. Questionairing to patients under enteral nutrition in Okinawa Prefecture (Second Report) Expectation of actual conditions of trace element deficiency in view of liquid diet used", Intravenous Enteral Alimentation, vol. 17, No. 1, p. 92, 2002, (with English translation).

Aiwa Maehara, et al., "18. Effects of trace element-rich liquid diet F2α on trace element deficiency and influence by its prolonged administration", Intravenous Enteral Alimentation, vol. 17, No. 1, p. 92, 2002, (with English translation).

Sayuri Yamashiro, et al, "19. Effects of trace element-rich liquid diet K4S on trace element deficiency with patients under prolonged enteral nutrition", Intravenous Enteral Alimentation, vol. 17, No. 1, p. 93, 2002, (with English translation).

Kazumi Uechi, et al., "110. Questionnaring to Patients under enteral nutrition in Okinawa Prefecture (Second Report)-Changes in actual conditions before and after the enforcement of care insurance-" Intravenous Enteral Alimentation, vol. 17, No. 1, p. 138, 2002, (with English translation).

Kiyoshi Wakugami, et al., "Effect of ISO--CZ-and evaluation of daily copper requirement for patients with long-term enteral nutrition", JJPEN, vol. 23, No. 3, 2001, pp. 179-183, (with English translation).

Rinshô Eiyô (Clinical Nutrition), vol. 103, No. 4, 2003.9 (Special Number) (with English translation), pp. 424-431.

* cited by examiner ically contribuent to elderly bedsores include multiple complications such

TOTAL ENTERAL NUTRITIOUS COMPOSITION

CROSS-REFERENCE TO RELATED APPLICATION

The present application is a continuation of PCT/JP2005/017379, filed on Sep. 21, 2005, which claims priority to Japanese Patent Application No. 2004-275527, filed on Sep. 22, 2004, and Japanese Patent Application No. 2004-348106, filed on Dec. 1, 2004: the entire contents of these applications are incorporated herein by reference.

BACKGROUND OF THE INVENTION

1. Field of the Invention

The present invention relates to a total enteral nutritious composition that can efficiently supply proteins, fats, sugars, vitamins and minerals to those in need of nutritional supplementation, such as the elderly or inpatients.

2. Related Background Art

Concerns have been raised in recent years regarding the deteriorating nutritional state of elderly inpatients and the elderly cared for at home. A malnutritional state characterized by protein and energy deficiency is known as Protein Energy Malnutrition (PEM), and the importance of effective nutritional supplementation for this state is well recognized. In "Study of Nutritional Management Services for the Elderly" for 1995-1998 (1999 Health and Welfare Ministry Report, Matsuda, A. et al.), it was observed that individuals at risk of PEM, having serum levels of below 3.5 g/dL for the nutritional index albumin, consisted of approximately 40% elderly inpatients and approximately 30% home cared patients. A lack of sufficient protein and energy due to reduced dietary intake or the like can produce a serious malnutritional state, resulting in immune depression-related infection, loss of muscular strength and a bedridden state, and leading to extended hospitalization and increased medical costs. A bedridden condition often causes bedsores, of which contributing factors include lack of energy, insufficient protein intake, impaired biosynthesis of protein, reduced fat intake and lack of trace elements such as zinc (Rinsho Eiyo: Vol. 103, No. 4, pp. 424-431, 2003). Some factors characteristically contributing to elderly bedsores include multiple complications such as angiopathy, anorexia, and immune impairment due to malnutrition (Rinsho Eiyo: Vol. 103, No. 4, pp. 424-431, 2003).

An oral nutritious composition comprehensively comprising proteins, fats, sugars, vitamins and minerals for individuals requiring nutritional supplementation is known (Japanese Patent Publication No. 3102645). The nutritious composition alone can provide nutritional management, and it is characterized by containing milk protein and soybean protein in a specific proportion among the protein materials in the composition, as well as containing ω-3 fatty acids and ω-6 fatty acids in a specific ratio among the fats. There is also known a total enteral nutrient preparation comprising proteins, fats, sugars, an emulsifier and water, which has a specified osmotic pressure and amino acid score (Japanese Patent Laid-open (Kokai) Publication No. 2004-51494).

The elderly and patients suffering considerable malnutrition have lower gastric volume, which limits the amount of food that can be ingested. Such individuals require enteral nutritious compositions with high caloric content per consumption volume, an optimal balance of nutrients and high concentrations of components such as vitamins and minerals. Enteral nutritious compositions with 100 kcal per 100 mL are available on the market, and demand is expected to further increase in the future.

At the current time, however, no enteral nutrient preparation is known that improves serum levels of the nutritional index albumin, maintains suitable blood levels of copper, zinc and sodium and has an ameliorating effect on bedsores. Moreover, from the comprehensive viewpoint of incorporating highly purified proteins and fats and including an appropriate dosage of vitamins to facilitate energy production in the body, no total enteral nutritious composition has yet been provided that comprises an appropriate formulation of these essential components. For example, merely increasing the sodium content of a protein-rich nutritious composition has been a limited strategy due to protein precipitation (salting out). However, since some elderly suffer from hyponatremia, it is very important to increase the sodium content with protein content in high-energy total enteral nutritious compositions.

[Patent document 1] Japanese Patent Publication No. 3102645

[Patent document 2] Japanese Patent Laid-open (Kokai) Publication No. 2004-51494

SUMMARY OF THE INVENTION

Problems to be Solved by the Invention

It is an object of the invention to provide an improved total enteral nutritious composition which is by itself capable of supplying total required nutrition to individuals unable to obtain sufficient nutrition from eating, such as the elderly or inpatients. More specifically, the object is to provide a total enteral nutritious composition appropriately incorporating proteins, fats, sugars, vitamins and minerals, and especially zinc and copper, and exhibiting a notable effect toward improving serum levels of the nutritional index albumin and improving the condition of bedsores. It is a further object to provide a novel total enteral nutritious composition with a maximized protein content, incorporation of a sufficient dosage of sodium to prevent protein precipitation and high vitamin B1 and vitamin B2 contents, to provide an efficient restoration effect on nutritional state, prevent malnutrition and ameliorate and prevent bedsores.

Means for Solving the Problems

The total enteral nutritious composition of the invention achieves these objects by incorporating proteins, sugars, fats, minerals and vitamins and combining the following three general features.

(1) A copper content of no greater than 0.15 mg, and a zinc/copper weight ratio of 10-25, preferably 13-20, and most preferably 15-18, per 100 kcal of the composition. In this case, the zinc content is preferably at least 1.5 mg and the copper content is preferably 0.075-0.15 mg. This is based on the knowledge that a high copper content inhibits zinc absorption.

(2) A sodium content of 185 mg or greater, and a protein content of preferably 4.0 g or greater and more preferably 5.0 g or greater, per 100 kcal of the composition. This is because a high sodium concentration is necessary to prevent sodium deficiency. Even with such a high sodium concentration, if the main sodium sources used are sodium phosphate and sodium citrate, it is possible to prevent problems caused by protein precipitation due to salting out when the protein concentration is high.

(3) A vitamin B1 content of at least 0.3 mg and a vitamin B2 content of at least 0.25 mg, per 100 kcal of the composition. By thus including high concentrations of vitamin B1 which is necessary for energy production from sugars and vitamin B2 which is necessary for energy production from fats, it is possible to achieve more efficient energy production.

More specifically, the zinc content is preferably 1.5-3.0 mg, the copper content is preferably 0.075-0.15 mg and the sodium content is preferably 185-385 mg, per 100 kcal of the composition. More preferred is a zinc content of 1.8-3.0 mg, a copper content of 0.09-0.12 mg and a sodium content of 200-385 mg, per 100 kcal of the composition.

In order to aid combustion of sugars and fats in the body, the vitamin B1 content is preferably 0.4-2 mg and the vitamin B2 content is preferably 0.25-2.0 mg per 100 kcal of the composition, which are higher vitamin contents than is customary. As additional vitamins, there are preferably incorporated vitamin B6 at 0.30 mg or greater and preferably 0.5-2.0 mg, and biotin at 1.0 µg or greater and preferably 1.0-10 µg. A more desirable effect may be obtained by adding 0.20-0.70 µg of vitamin B12, 20-80 µg of folic acid, 100-450 µg of β-carotene and 10-70 mg of vitamin C per 100 kcal.

The energy sources for the total enteral nutritious composition of the invention are proteins, sugars and fats. The proportion of energy supplied by the proteins, sugars and fats is preferably adjusted in a range of 10-40% from proteins, 40-80% from sugars and 10-40% from fats.

Protein is incorporated at preferably 4.0 g or greater and more preferably 5.0 g or greater per 100 kcal of the composition. The protein source may be either animal protein or vegetable protein, but it is preferably a mixture of animal and vegetable protein in a ratio of between 4:1 and 1:4. It preferably also contains as protein glutamine or glutamine peptides, and soybean protein or its hydrolysate. The total glutamine in the protein is preferably at least 0.6 g per 100 kcal of the composition. Most preferably, the ratio of glutamine or glutamine peptides to soybean protein or its hydrolysate is between 4:1 and 1:4.

The fat source used may be absorbable animal or vegetable fats. The fats preferably include at least 35 wt % medium-chain fatty acid oils, and the ratio of ω-3 fatty acids to ω-6 fatty acids in the fats is preferably between 1:10 and 1:1. Also, the medium-chain fatty acid triglycerides preferably constitute 40-65 wt % of the fats, with a ratio of ω-3 fatty acids to ω-6 fatty acids in the fats of between 1:4 and 1:1. Medium-chain fatty acids are C6-12 fatty acids, and because of their high absorption rate they are suitable as dietetic foods for the elderly and inpatients.

The sugar source used may be dextrin, oligosaccharides, sucrose, glucose or fructose, either alone or in combinations.

In addition to the components mentioned above, the essential amino acids leucine, isoleucine, valine, threonine, lysine, methionine, phenylalanine and tryptophan may also be added as necessary. As minerals there may be added as necessary sodium, zinc and copper mentioned above, as well as calcium, iron, phosphorus, magnesium, potassium, iodine, manganese, selenium, chromium, molybdenum and the like.

The total enteral nutritious composition of the invention may be administered orally or by tube. A fluid liquid composition is preferred for this purpose, in which case the viscosity of the composition is preferably in the range of 6-18 mPa·s (25° C.).

EFFECT OF THE INVENTION

The total enteral nutritious composition of the invention exhibits notable effects including treatment or prevention of human Protein Energy Malnutrition (PEM), amelioration of serum albumin levels, amelioration of bedsores, improvement of albumin/globulin ratios, improvement of reduced sodium and chloride contents, improvement of hemoglobin levels, improvement of hematocrit, increase in serum zinc content and increase in peripheral lymphocyte count.

DESCRIPTION OF THE PREFERRED EMBODIMENTS

The protein source used for the total enteral nutritious composition of the invention is purified animal protein or vegetable protein, or a combination thereof. Particularly for persons with cerebrovascular disease or hyperlipidemia, intake with consideration of the ratio of animal proteins and vegetable proteins among the balance of nutrients is important for preventing arteriosclerosis and lowering blood lipids, and for the total enteral nutritious composition of the invention an animal protein:vegetable protein ratio of between 1:4 and 4:1 is recommended. Furthermore, since it has been confirmed that patient systemic or enteric immunity is enhanced by compositions rich in glutamine, which has attracted interest as an immune-boosting nutrient, addition of glutamine or glutamine peptides derived from wheat gluten hydrolysate, or purified glutamine forms such as alanylglutamine or glycylglutamine, is recommended for those who require it. The total glutamine content in the composition of the invention is preferably at least 0.6 g per 100 kcal.

The fat used in the total enteral nutritious composition of the invention may be any fat source ingestible by humans. When highly efficient energy supplementation is necessary, recommended fats are those comprising in the molecular structure medium-chain fatty acid triglycerides, medium-chain fatty acid diglycerides or medium-chain fatty acids, which have enteric absorption rates comparable to glucose and have high energy production efficiency. Incorporating ω-3 fatty acids such as eicosapentaenoic acid or α-linolenic acid, which exhibit anti-inflammatory effects, is useful for individuals in need of active administration of such fats, e.g. patients with inflammation or patients requiring protection from inflammation. The total enteral nutritious composition of the invention preferably contains medium-chain fatty acid oils constituting at least 35 wt % of the total fats, and the ratio of ω-3 fatty acids to ω-6 fatty acids in the fat is preferably between 1:10 and 1:1.

Mineral requirements are normally established based on the 6th Edition of Recommended Dietary Allowances for Japanese. However, because hyponatremia is a problem in the elderly due to reduced consumption, the total enteral nutritious composition of the invention is fortified with sodium. The sodium source may be any one that can be ingested by or administered to humans, but sodium citrate and sodium phosphate are used as primary sodium sources to prevent precipitation of proteins by salting out. According to the invention, an effect is exhibited if the sodium content is 185 mg or greater per 100 kcal, but the effect is more notable at 200-385 mg per 100 kcal.

Zinc plays a major role in the function and structure of numerous enzymes in the body, and is deficient in individuals in a poor nutritional condition. Zinc supplementation increases blood zinc levels and is useful for individuals with wounds such as bedsores, or those at risk of them. Because absorption of zinc is competitive with divalent copper ion, the proportion of copper and zinc and the copper content must be adjusted to favor absorption of zinc. In the total enteral nutritious composition of the invention, zinc is added to at least 1.5 mg and preferably 1.5-3.0 mg and copper at 0.075-0.15 mg per 100 kcal, with a zinc/copper weight ratio of 10-25, preferably 13-20, even more preferably 15-18 and most preferably 15, in order to obtain an effect of promoting healing of wounds such as bedsores. According to the 6th Edition of Recommended Dietary Allowances for Japanese, the zinc/copper weight ratio differs depending on age and gender, being approximately 6.7 for the highest group of males aged 30-49 and approximately 6.3 and 6.4 for elderly males and females, respectively; thus, zinc deficiency in malnutrition requires the zinc content to be increased further above the copper content than normal. For inflammation in individuals requiring nutritional supplementation, addition of the antioxidant trace element selenium at about 4.5-18 μg per 100 kcal is effective.

Vitamins are important as essential coenzymes for bioactivity including energy production, protein metabolism, skin and mucous membrane physiological function and the like. However, the dosages of vitamins to be added for malnourished individuals have not been sufficiently studied. In the total enteral nutritious composition of the invention, vitamin B1 is added to at least 0.3 mg, vitamin B2 is added to at least 0.25 mg, vitamin B6 is added to at least 0.3 mg and biotin is added to at least 1.0 μg, per 100 kcal. The most effective formulation is vitamin B1 at 0.4-2.0 mg, vitamin B2 at 0.25-2.0 mg, vitamin B6 at 0.5-2.0 mg and biotin at 1.0-10 μg per 100 kcal. Addition of other vitamins is also effective for nutrition amelioration or maintenance, prevention of malnutrition, treatment or prevention of bedsores and treatment or prevention of anemia. It is recommended to include in the total enteral nutritious composition of the invention vitamin B12, folic acid, β-carotene, vitamin C and the like, which have anti-inflammatory effects, antioxidant effects and bedsore-preventing effects. Specifically, for example, vitamin B12 is added to 0.20-0.7 μg, folic acid is added to 20-80 μg, β-carotene is added to 100-450 μg and vitamin C is added to 10-70 mg, per 100 kcal of the total enteral nutritious composition of the invention. These added vitamins may be from any starting materials ingestible by humans, and no restrictions are placed on their sources.

The total enteral nutritious composition of the invention may also contain suitable flavorings or non-calorie sweeteners such as aspartame to aid in oral ingestion. Components such as non-digestible dietary fiber to promote evacuation, or in certain cases orally administrable medicines, may also be added as necessary in ranges that do not inhibit the function of the total enteral nutritious composition of the invention.

Malnourished individuals are often unable to easily ingest food, in which cases a tube may be used for active nutritional supplementation. However, it has not been possible in the prior art to include necessary protein in a high proportion as according to the invention, while adequate addition of minerals results in precipitation and increased liquid viscosity, making administration by tube impossible. As a result of experimenting with ingredient proportions and preparation methods, a low-viscosity liquid total enteral nutritious composition was obtained which allows administration by tube for the first time. The viscosity of the composition is in the range of 6-18 mPa·s (25° C.), and the flow properties are excellent.

The total enteral nutritious composition of the invention is provided for individuals in a malnourished state, and is particularly effective for individuals suffering from Protein Energy Malnutrition (PEM), hypoalbuminemia, hyponatremia, zinc deficiency, anemia, reduced hemoglobin and hematocrit, bedsores or wounds and impaired immunological competence. The total enteral nutritious composition of the invention therefore provides a major contribution to such persons for which an effective composition has not existed in the prior art.

EXAMPLES

Example 1

Preparation of Total Enteral Nutritious Composition
(Composition 1)

A nutrient composition Table 1 was devised with consideration given to the optimal nutritive effect for malnutrition. The composition was formulated as a liquid composition having the material formulation shown in Table 2. A liquid total enteral nutritious composition was prepared by a process in which a sodium starting material was combined with a protein starting material and emulsifying agent in the amounts listed in the table and emulsification was carried out several times using a high-pressure emulsifier at a pressure of 500-1,000 kg/cm$^2$, in order to obtain a composition with excellent emulsion stability and no precipitation of protein, etc. Specifically, the starting materials were repeatedly subjected to high-pressure emulsification with water using a high-pressure emulsifier, to prepare an emulsion with a satisfactory concentration of 1 kcal/ml. The ratio of animal protein to vegetable protein was 1:1.5. The proportion of glutamine peptide to soybean protein or its hydrolysate was 1:1.4, and the ratio of ω-3 fatty acids to ω-6 fatty acids in the fatty acid composition was 1:3. The composition was filled into an aluminum package using an ordinary filling machine and placed in a retort pasteurizer for sterilization under ordinary conditions. The solution components were stable and the viscosity was 9 mPa·s (25° C.) even after one year.

TABLE 1

Table 1: Nutrient composition 1

| | | |
|---|---|---|
| Calories | kcal | 100 |
| Protein | g | 5.5 |
| | Containing glutamine g | 0.95 |
| Fat | g | 2.78 |
| Medium-chain fatty acid oils | g | 1.39 |
| Sugars | g | 12.5 |
| Sodium | mg | 200 |
| Calcium | mg | 70 |
| Iron | mg | 1.2 |
| Phosphorus | mg | 70 |
| Magnesium | mg | 32 |
| Potassium | mg | 200 |
| Copper | mg | 0.12 |
| Iodine | μg | 15 |
| Manganese | mg | 0.4 |
| Selenium | μg | 9 |
| Zinc | mg | 1.8 |
| Chromium | μg | 3 |
| Molybdenum | μg | 3 |
| Vitamin A | μg RE | 111 |
| Retinol | μg | 51 |
| β-Carotene | μg | 360 |
| Vitamin D | μg | 0.6 |
| Vitamin E | mg α-TE | 3 |
| Vitamin K | μg | 5.5 |
| Vitamin B1 | mg | 0.6 |
| Vitamin B2 | mg | 0.36 |
| Niacin | mg NE | 2.4 |
| Vitamin B6 | mg | 0.6 |
| Folic acid | μg | 60 |
| Vitamin B12 | μg | 0.5 |
| Biotin | μg | 3.0 |

TABLE 1-continued

Table 1: Nutrient composition 1

| | | |
|---|---|---|
| Pantothenic acid | mg | 1.5 |
| Vitamin C | mg | 40 |

TABLE 2

Table 2: Starting material composition 1

| Ingredient | Content (in 100 mL) | Units |
|---|---|---|
| Casein sodium | 3.878 | g |
| Glutamine peptide (wheat gluten decomposition product) | 1.666 | g |
| Powdered soybean protein | 1.109 | g |
| L-Lysine hydrochloride | 0.030 | g |
| L-Tryptophan | 0.010 | g |
| Medium-chain triglycerides | 1.390 | g |
| Edible oils/fats and refined fish oil | 1.055 | g |
| Maltodextrin, dietary fiber, oligosaccharide | 14.131 | g |
| Sodium citrate | 0.413 | g |
| Disodium phosphate | 0.259 | g |
| Magnesium chloride | 0.223 | g |
| Potassium citrate | 0.170 | g |
| Calcium chloride | 0.119 | g |
| Potassium carbonate | 0.200 | g |
| Calcium carbonate | 0.076 | g |
| Calcium lactate | 0.019 | g |
| Sodium ferrous citrate | 9.545 | mg |
| Trace element yeast MIX (containing zinc, copper, manganese, chromium, molybdenum, selenium, iodine) | 55.748 | mg |
| Sodium L-ascorbate | 0.072 | g |
| Vitamin E | 5.751 | mg |
| β-Carotene preparation | 1.300 | mg |
| Menaquinone powder | 2.751 | mg |
| Nicotinic acid amide | 1.690 | mg |
| Calcium pantothenate | 1.794 | mg |
| Thiamine hydrochloride | 0.960 | mg |
| Vitamin A fatty acid ester preparation | 1.052 | mg |
| Pyridoxine hydrochloride | 0.728 | mg |
| Sodium riboflavin 5'-phosphate | 0.449 | mg |
| Vitamin D3 | 0.129 | mg |
| Folic acid | 0.063 | mg |
| Biotin | 2.551 | µg |
| Cyanocobalamin | 0.550 | µg |
| Emulsifier | 0.335 | g |
| Sweetener | 7.350 | mg |
| Flavoring | 0.103 | g |

Example 2

Preparation of Total Enteral Nutritious Composition (Composition 2)

The nutrient composition listed in Table 3 was prepared in the same manner as Example 1. The composition was formulated as a liquid composition having the material formulation shown in Table 4. As in Example 1, a sodium starting material was combined with a protein starting material and emulsifying agent in the amounts listed in the table and emulsification was carried out several times using a high-pressure emulsifier at a pressure of 500-1,000 kg/cm², to prepare a liquid total enteral nutritious composition. Specifically, the starting materials were repeatedly subjected to high-pressure emulsification with water using a high-pressure emulsifier, to prepare an emulsion with a satisfactory concentration of 1 kcal/ml. The ratio of animal protein to vegetable protein was 1:2. The proportion of glutamine peptide to soybean protein hydrolysate was 3:1, and the ratio of ω-3 fatty acids to ω-6 fatty acids in the fatty acid composition was 1:1. The composition was filled into an aluminum package using an ordinary filling machine and placed in a retort pasteurizer for sterilization under ordinary conditions. The solution components were stable and the viscosity was 16 mPa·s (25° C.) even after one year.

TABLE 3

Table 3: Nutrient composition 2

| | | |
|---|---|---|
| Calories | kcal | 100 |
| Protein | g | 6.0 |
| | Containing glutamine g | 1.05 |
| Fat | g | 2.78 |
| Medium-chain fatty acid oils | g | 1.80 |
| Sugars | g | 12.5 |
| Sodium | mg | 300 |
| Calcium | mg | 70 |
| Iron | mg | 1.2 |
| Phosphorus | mg | 70 |
| Magnesium | mg | 32 |
| Potassium | mg | 200 |
| Copper | mg | 0.13 |
| Iodine | µg | 15 |
| Manganese | mg | 0.4 |
| Selenium | µg | 9 |
| Zinc | mg | 3.0 |
| Chromium | µg | 3 |
| Molybdenum | µg | 3 |
| Vitamin A  Retinol | µg | 51 |
| β-Carotene | µg | 450 |
| Vitamin D | µg | 0.6 |
| Vitamin E | mg α-TE | 3 |
| Vitamin K | µg | 5.5 |
| Vitamin B1 | mg | 2.0 |
| Vitamin B2 | mg | 2.0 |
| Niacin | mg NE | 2.4 |
| Vitamin B6 | mg | 0.6 |
| Folic acid | µg | 80 |
| Vitamin B12 | µg | 0.5 |
| Biotin | µg | 8.0 |
| Pantothenic acid | mg | 1.5 |
| Vitamin C | mg | 70 |

TABLE 4

Table 4: Starting material composition 2

| Ingredient | Content (in 100 mL) | Units |
|---|---|---|
| Casein sodium | 2.301 | g |
| Glutamine peptide (wheat gluten decomposition product) | 3.876 | g |
| Powdered soybean protein | 1.321 | g |
| L-Lysine hydrochloride | 0.030 | g |
| L-Tryptophan | 0.010 | g |
| Medium-chain triglycerides | 1.800 | g |
| Edible oils/fats and refined fish oil | 0.980 | g |
| Maltodextrin, dietary fiber, oligosaccharide | 14.131 | g |
| Sodium citrate | 0.620 | g |
| Disodium phosphate | 0.388 | g |
| Magnesium chloride | 0.223 | g |
| Potassium citrate | 0.170 | g |
| Calcium chloride | 0.119 | g |
| Sodium hydroxide | 0.084 | g |
| Potassium carbonate | 0.200 | g |
| Calcium carbonate preparation | 0.076 | g |
| Calcium lactate | 0.019 | g |

TABLE 4-continued

Table 4: Starting material composition 2

| Ingredient | Content (in 100 mL) | Units |
|---|---|---|
| Sodium ferrous citrate | 14.317 | mg |
| Trace element yeast MIX (containing zinc, copper, manganese, chromium, molybdenum, selenium, iodine) | 78.111 | mg |
| Sodium L-ascorbate | 0.126 | g |
| Vitamin E | 5.751 | mg |
| β-Carotene preparation | 1.625 | mg |
| Menaquinone powder | 2.751 | mg |
| Nicotinic acid amide | 1.690 | mg |
| Calcium pantothenate | 1.794 | mg |
| Thiamine hydrochloride | 3.168 | mg |
| Vitamin A fatty acid ester preparation | 1.052 | mg |
| Pyridoxine hydrochloride | 0.728 | mg |
| Sodium riboflavin 5'-phosphate | 0.808 | mg |
| Vitamin D3 | 0.129 | mg |
| Folic acid | 0.084 | mg |
| Biotin | 8.498 | μg |
| Cyanocobalamin | 0.550 | μg |
| Emulsifier | 0.335 | g |
| Sweetener | 7.350 | mg |
| pH adjuster | q.s. | |
| Flavoring | 0.103 | g |

Example 3

Preparation of Total Enteral Nutritious Composition (Composition 3)

The nutrient composition listed in Table 5 was prepared in the same manner as Example 1. The composition was formulated as a liquid composition having the material formulation shown in Table 6. As in Example 1, a sodium starting material was combined with a protein starting material and emulsifying agent and emulsification was carried out several times using a high-pressure emulsifier at a pressure of 500-1,000 kg/cm$^2$, to prepare a liquid total enteral nutritious composition. Specifically, the starting materials were repeatedly subjected to high-pressure emulsification with water using a high-pressure emulsifier, to prepare an emulsion with a satisfactory concentration of 1 kcal/ml. The composition was filled into an aluminum package using an ordinary filling machine and placed in a retort pasteurizer for sterilization under ordinary conditions. The solution components were stable and the viscosity was 10 mPa·s (25° C.) even after one year.

TABLE 5

Table 5: Nutrient composition 3

| | | |
|---|---|---|
| Calories | kcal | 100 |
| Protein | g | 5.0 |
| Containing glutamine | g | 0.60 |
| Fat | g | 2.78 |
| Medium-chain fatty acid oils | g | 0.97 |
| Sugars | g | 12.5 |
| Sodium | mg | 185 |
| Calcium | mg | 70 |
| Iron | mg | 1.2 |
| Phosphorus | mg | 70 |
| Magnesium | mg | 32 |
| Potassium | mg | 200 |
| Copper | mg | 0.15 |
| Iodine | μg | 15 |
| Manganese | mg | 0.4 |
| Selenium | μg | 9 |
| Zinc | mg | 1.6 |
| Chromium | μg | 3 |
| Molybdenum | μg | 3 |
| Vitamin A   Retinol | μg | 51 |
| β-Carotene | μg | 105 |
| Vitamin D | μg | 0.6 |
| Vitamin E | mg α-TE | 3 |
| Vitamin K | μg | 5.5 |
| Vitamin B1 | mg | 0.3 |
| Vitamin B2 | mg | 0.25 |
| Niacin | mg NE | 2.4 |
| Vitamin B6 | mg | 0.5 |
| Folic acid | μg | 24 |
| Vitamin B12 | μg | 0.5 |
| Biotin | μg | 1.0 |
| Pantothenic acid | mg | 1.5 |
| Vitamin C | mg | 12 mg |

TABLE 6

Table 6: Starting material composition 3

| Ingredient | Content (in 100 mL) | Units |
|---|---|---|
| Casein sodium | 3.767 | g |
| Glutamine peptide (Ala-Gln) | 0.908 | g |
| Powdered soybean protein | 1.081 | g |
| L-Lysine hydrochloride | 0.030 | g |
| L-Tryptophan | 0.010 | g |
| Medium-chain triglycerides | 0.97 | g |
| Edible oils/fats and refined fish oil | 1.810 | g |
| Maltodextrin, dietary fiber, oligosaccharide | 14.131 | g |
| Sodium citrate | 0.383 | g |
| Disodium phosphate | 0.240 | g |
| Magnesium chloride | 0.223 | g |
| Potassium citrate | 0.170 | g |
| Calcium chloride | 0.119 | g |
| Potassium carbonate | 0.200 | g |
| Calcium carbonate | 0.076 | g |
| Calcium lactate | 0.019 | g |
| Sodium ferrous citrate | 8.859 | mg |
| Trace element yeast MIX (containing zinc, copper, manganese, chromium, molybdenum, selenium, iodine) | 52.111 | mg |
| Sodium L-ascorbate | 0.0216 | g |
| Vitamin E | 5.751 | mg |
| β-Carotene preparation | 0.379 | mg |
| Menaquinone powder | 2.751 | mg |
| Nicotinic acid amide | 1.690 | mg |
| Calcium pantothenate | 1.794 | mg |
| Thiamine hydrochloride | 0.480 | mg |
| Vitamin A fatty acid ester preparation | 1.052 | mg |
| Pyridoxine hydrochloride | 0.606 | mg |
| Sodium riboflavin 5'-phosphate | 0.312 | mg |
| Vitamin D3 | 0.129 | mg |
| Folic acid | 0.025 | mg |
| Biotin | 0.849 | μg |
| Cyanocobalamin | 0.550 | μg |
| Emulsifier | 0.330 | g |
| Sweetener | 7.350 | mg |
| Flavoring | 0.103 | g |

Example 4

Preparation of Total Enteral Nutritious Composition (Composition 4)

The nutritive composition listed in Table 7 was prepared in the same manner as Example 1. The composition was formulated as a liquid composition having the material formulation shown in Table 8. As in Example 1, a sodium starting material was combined with a protein starting material and emulsifying agent and emulsification was carried out several times using a high-pressure emulsifier at a pressure of 500-1,000 kg/cm$^2$, to prepare a liquid total enteral nutritious composition. Specifically, the starting materials were repeatedly subjected to high-pressure emulsification with water using a high-pressure emulsifier, to prepare an emulsion with a satisfactory concentration of 1 kcal/ml. The composition was filled into an aluminum package using an ordinary filling machine and placed in a retort pasteurizer for sterilization under ordinary conditions. The solution components were stable and the viscosity was 8 mPa·s (25° C.) even after one year.

TABLE 7

Table 7: Nutrient composition 4

| Ingredient | Units | Content |
|---|---|---|
| Calories | kcal | 100 |
| Protein | g | 5.5 |
| Containing glutamine | g | 0.95 |
| Fat | g | 2.78 |
| Medium-chain fatty acid oil | g | 1.39 |
| Sugars | g | 12.5 |
| Sodium | mg | 245 |
| Calcium | mg | 70 |
| Iron | mg | 1.2 |
| Phosphorus | mg | 70 |
| Magnesium | mg | 32 |
| Potassium | mg | 200 |
| Copper | mg | 0.09 |
| Iodine | μg | 15 |
| Manganese | mg | 0.4 |
| Selenium | μg | 9 |
| Zinc | mg | 1.6 |
| Chromium | μg | 3 |
| Molybdenum | μg | 3 |
| Vitamin A | μg RE | 111 |
| Retinol | μg | 51 |
| β-Carotene | μg | 285 |
| Vitamin D | μg | 0.6 |
| Vitamin E | mg α-TE | 3 |
| Vitamin K | μg | 5.5 |
| Vitamin B1 | mg | 0.4 |
| Vitamin B2 | mg | 0.36 |
| Niacin | mg NE | 2.4 |
| Vitamin B6 | mg | 0.6 |
| Folic acid | μg | 60 |
| Vitamin B12 | μg | 0.5 |
| Biotin | μg | 3.0 |
| Pantothenic acid | mg | 1.5 |
| Vitamin C | mg | 40 |

TABLE 8

Table 8: Starting material composition 4

| Ingredient | Content (in 100 mL) | Units |
|---|---|---|
| Casein sodium | 3.878 | g |
| Glutamine peptide (wheat gluten decomposition product) | 1.666 | g |
| Powdered soybean protein | 1.109 | g |
| L-Lysine hydrochloride | 0.030 | g |
| L-Tryptophan | 0.010 | g |
| Medium-chain triglycerides | 1.390 | g |
| Edible oils/fats and refined fish oil | 1.055 | g |
| Maltodextrin, dietary fiber, oligosaccharide | 14.131 | g |
| Sodium citrate | 0.413 | g |
| Disodium phosphate (crystal) | 0.259 | g |
| Magnesium chloride | 0.223 | g |
| Potassium citrate | 0.170 | g |
| Calcium chloride | 0.119 | g |
| Potassium carbonate | 0.200 | g |
| Calcium carbonate preparation | 0.076 | g |
| Calcium lactate | 0.019 | g |
| Sodium ferrous citrate | 9.545 | mg |
| Sodium chloride | 114.50 | mg |
| Trace element yeast MIX (containing zinc, copper, manganese, chromium, molybdenum, selenium, iodine) | 50.051 | mg |
| Sodium L-ascorbate | 0.072 | g |
| Vitamin E | 5.751 | mg |
| β-Carotene preparation | 1.027 | mg |
| Menaquinone powder | 2.751 | mg |
| Nicotinic acid amide | 1.690 | mg |
| Calcium pantothenate | 1.794 | mg |
| Thiamine hydrochloride | 0.640 | mg |
| Vitamin A fatty acid ester preparation | 1.052 | mg |
| Pyridoxine hydrochloride | 0.728 | mg |
| Sodium riboflavin 5'-phosphate | 0.449 | mg |
| Vitamin D3 | 0.129 | mg |
| Folic acid | 0.063 | mg |
| Biotin | 2.551 | μg |
| Cyanocobalamin | 0.550 | μg |
| Emulsifier | 0.335 | g |
| Sweetener | 7.350 | mg |
| Flavoring | 0.103 | g |

[Efficacy Test 1]

Human Test

The liquid total enteral nutritious composition of the invention prepared in Example 1 (invention product) was used to examine the ameliorating effect on nutritional state in elderly PEM patients. The subjects were nine hospitalized elderly nutrition-managed (tube-fed) PEM patients with albumin levels of 3.5 g/dL or lower, with a mean age of 81.3±9.9. The administration period was eight weeks. Commercially available nutritive products A, B, etc. were administered prior to administration of the invention product. The replenishment rates for the commercially available nutritive products A, B, etc. and the nutrient dosages in the invention product are shown in Table 9. The energy supplied by the invention product (873±124 kcal/day) was equivalent to the average energy supplied by the previously administered commercially available nutritive products A, B, etc. (863±133 kcal/day). The nutritional condition was confirmed during administration of the commercially available nutritive products A, B, etc. and during administration of the invention product. Hematological examination and biochemical blood profile examination were conducted by early morning blood sampling before, 4 weeks after and 8 weeks after start of the test.

TABLE 9

Table 9. Nutrient dosages and replenishment rates

| | Recommended allowance | | Commercial nutritive product (average) | | Invention product | | P value with commercial nutritive product |
|---|---|---|---|---|---|---|---|
| | Male | Female | Mean (S.D.) | Replenishment rate (%) | Mean (S.D.) | Replenishment rate (%) | |
| Energy (kcal) | 1600 | 1300 | 863 ± 133 | 65% | 873 ± 124 | 65% | 0.5738 |
| Protein (g) | 65 | 55 | 39.6 ± 6.5 | 70% | 48.0 ± 6.8 | 85% | 0.0000*** |
| Fat (g) | 35.6 | 28.9 | 23.2 ± 5.6 | 78% | 24.2 ± 3.4 | 81% | 0.3052 |
| Sugar (g) | 254.9 | 205.0 | 124.3 ± 17.3 | 59% | 122.2 ± 17.3 | 58% | 0.4141 |
| Sodium (mg) | — | — | 1276 ± 321 | — | 1745 ± 247 | — | 0.0000*** |
| Potassium (mg) | 2000 | 2000 | 1043 ± 183 | 52% | 1745 ± 247 | 87% | 0.0000*** |
| Calcium (mg) | 600 | 600 | 462 ± 150 | 77% | 611 ± 87 | 102% | 0.0009*** |
| Magnesium (mg) | 280 | 240 | 191 ± 61 | 78% | 279 ± 40 | 114% | 0.0000*** |
| Phosphorus (mg) | 700 | 700 | 487 ± 83 | 70% | 611 ± 87 | 87% | 0.0000*** |
| Iron (mg) | 10 | 10 | 7.7 ± 1.8 | 77% | 10.5 ± 1.5 | 105% | 0.0000*** |
| Zinc (mg) | 10 | 9 | 7.3 ± 2.7 | 80% | 15.7 ± 2.2 | 172% | 0.0000*** |
| Copper (mg) | 1.6 | 1.4 | 0.89 ± 0.36 | 62% | 1.05 ± 0.15 | 74% | 0.0655 |
| Zinc/copper | | | 8.2 | | 14.9 | | |
| Retinol (µg) | — | — | 421 ± 119 | — | 445 ± 63 | — | 0.4342 |
| Carotene (µg) | — | — | 73 ± 72 | — | 3142 ± 445 | — | 0.0000*** |
| Retinol equiv. (µg RE) | 600 | 540 | 533 ± 244 | 97% | 969 ± 137 | 177% | 0.0000*** |
| Vitamin D (µg) | 2.5 | 2.5 | 2.17 ± 1.48 | 87% | 4.36 ± 0.62 | 175% | 0.0000*** |
| Vitamin E (mg) | 10 | 8 | 11.2 ± 3.3 | 135% | 26.2 ± 3.7 | 317% | 0.0000*** |
| Vitamin K (µg) | 55 | 50 | 31.8 ± 21.1 | 63% | 48.0 ± 6.8 | 95% | 0.0019** |
| Vitamin B1 (mg) | 1.1 | 0.8 | 2.49 ± 4.10 | 298% | 5.24 ± 0.74 | 625% | 0.0271* |
| Vitamin B2 (mg) | 1.2 | 1 | 1.55 ± 1.53 | 151% | 3.14 ± 0.45 | 307% | 0.0026** |
| Niacin (mg) | 16 | 13 | 15.7 ± 7.8 | 118% | 20.9 ± 3.0 | 157% | 0.0392* |
| Vitamin B6 (mg) | 1.6 | 1.2 | 1.5 ± 0.8 | 122% | 5.2 ± 0.7 | 419% | 0.0000*** |
| Vitamin B12 (µg) | 2.4 | 2.4 | 3.7 ± 2.9 | 155% | 4.4 ± 0.6 | 182% | 0.4185 |
| Folic acid (µg) | 200 | 200 | 256 ± 178 | 128% | 524 ± 74 | 262% | 0.0002*** |
| Pantothenic acid (mg) | 5 | 5 | 7.2 ± 6.1 | 144% | 13.1 ± 1.9 | 262% | 0.0043** |
| Vitamin C (mg) | 100 | 100 | 106 ± 43 | 106% | 349 ± 49 | 349% | 0.0000*** |

*p < 0.05
**p < 0.01
***p < 0.001
Recommended allowances are according to "6th Edition of Recommended Dietary Allowances for Japanese" (standard values for ≧70 yrs of age).
Replenishment rates were determined based on averages of male/female loads of recommended allowances.

As a result of the test, patients with an albumin content of below 3.5 g/dL which is considered a PEM condition, exhibited a significant increase from an albumin level of 3.09±0.28 g/dL before beginning administration of the invention product, to 3.33±0.31 g/dL at 8 weeks. The albumin/globulin ratio also significantly increased from 0.8±0.2 at the start, to 0.9±0.2 at 8 weeks. Significant improvement was also found in sodium levels from 138±2.6 mmol/L at the start to 142±5.6 mmol/L at 8 weeks, in chloride levels from 102±4.1 mmol/L at the start to 107±4.7 mmol/L at 8 weeks, in hemoglobin levels from 12.0±1.5 g/dL at the start to 12.8±1.2 g/dL at 8 weeks and in hematocrit from 35.4±4.3% at the start to 38.1±3.7% at 8 weeks. The blood zinc levels significantly increased from 64±4 µg/dL at the start to 77±5 µg/dL at 8 weeks. Since the lower limit for standard serum zinc is 66 µg/dL (Rinsho Kensako Jiten, Ishiyaku Shuppan Publishing), levels were restored to normal even in this group with low zinc levels, thus demonstrating that the zinc content of the invention product was appropriate. In addition, the sizes of bedsores on patients with bedsores were significantly reduced after administration of the invention product. Peripheral lymphocyte counts, as an index of immune function, were also increased after administration. Although one case of mild diarrhea curable by administering intestinal remedy was observed among the nine subjects during the examination period, the incidence was only 11% and no other health problems were seen. Diarrhea is a major side-effect of enteral nutritive therapy, and in severe cases can require termination of therapeutic nutritional supplementation. Since the incidence of diarrhea with commercially available nutrient preparation C is 34% (according to the product package insert) and the incidence of diarrhea with commercially available nutrient preparation D is 17% (according to the product package insert), the invention product was clearly superior.

These results indicated that the total enteral nutritious composition of the invention comprises a suitable amount of protein for ameliorating the nutritional state of malnourished individuals. Furthermore, the total enteral nutritious composition of the invention can supply vitamins and trace elements in amounts required for energy metabolism, while electrolytes and trace elements such as sodium and zinc are also normalized, eliminating the need for addition of large amounts of salt as with conventional nutrient preparations. The total enteral nutritious composition of the invention used in this test was administered at an average daily dose of only 873 kcal while supplying proteins, vitamins, salt and trace elements, and it is therefore highly useful for improvement of malnutrition, hypoalbuminemia, anemia and bedsores.

The nutritious compositions 2, 3 and 4 prepared in Examples 2, 3 and 4 also exhibited efficacy by each indicator.

[Efficacy Test 2]
Therapeutic Effect on Human Bedsores

The liquid total enteral nutritious composition of the invention prepared in Example 1 (invention product) was used to examine the ameliorating effect on bedsores in an elderly patient with an intractable bedsore. The patient was a very elderly 95-year-old hospitalized patient who required an attendant. The patient had been malnourished for over two years with albumin of less than 3.5 mg/dL since July 2002 according to the earliest nutrition evaluation record. The patient had previously been diagnosed with arteriosclerosis obliterans (both legs, particularly the right) and had a bedsore on the right foot, first toe root; nutritional supplementation had been supplied with commercially available enteral nutritive product A. An in-house conference concluded that the bedsore would be difficult to heal with the current treatment. As poor circulation was considered to be the fundamental problem, the commercially available enteral nutritive product A and the invention product in an amount with the same calorie content were administered to the elderly patient with the intractable bedsore, and healing of the bedsore was measured. The nutrient dosages of the commercially available enteral nutritive product A and the invention product are shown in Table 10. The energy content was the same with administration of the commercially available enteral nutritive product A and administration of the invention product.

TABLE 10

Table 10. Nutrient dosages

|  | Commercial enteral nutritive product A | Invention product |
| --- | --- | --- |
| Energy (kcal) | 600 | 600 |
| Protein (g) | 24.0 | 33.0 |
| Fat (g) | 15.4 | 16.7 |
| Sugar (g) | 94.2 | 84.0 |
| Sodium (mg) | 618 | 1200 |
| Potassium (mg) | 954 | 1200 |
| Calcium (mg) | 360 | 420 |
| Magnesium (mg) | 120 | 192 |
| Phosphorus (mg) | 498 | 420 |
| Iron (mg) | 7.8 | 7.2 |
| Zinc (mg) | 6.0 | 10.8 |
| Copper (mg) | 0.90 | 0.72 |
| Zinc/copper ratio | 6.7 | 15.0 |
| Retinol equiv. (µg RE) | 540 | 666 |
| Vitamin D (µg) | 4.50 | 3.60 |
| Vitamin E (mg) | 12.0 | 18.0 |
| Vitamin K (µg) | 30.0 | 33.0 |
| Vitamin B1 (mg) | 1.14 | 3.60 |
| Vitamin B2 (mg) | 1.32 | 2.16 |
| Niacin (mg) | 11.58 | 14.40 |
| Vitamin B6 (mg) | 1.56 | 3.60 |
| Vitamin B12 (µg) | 2.4 | 3.0 |
| Folic acid (µg) | 300 | 360 |
| Pantothenic acid (mg) | 5.16 | 9.00 |
| Vitamin C (mg) | 60 | 240 |
| Biotin (mg) | — | 18.0 |

The bedsore was a 4 cm×4 cm oval prior to administration of the invention product, but by the second week after administration it had shrunk to a 3 cm×3 cm oval, demonstrating an obvious curative effect. The bedsore was observed to contain soft yellow necrotic tissue with minimal raised flesh before administration, and no improvement in the outer appearance was apparent with the commercially available nutritive product A. After administration of the invention product, however, formation of good quality flesh notably increased and the periphery of the bedsore changed from pink to white, thus showing clear improvement. The fact that a curative effect was clearly seen in this 95-year-old malnourished bedsore-afflicted patient within 2 weeks of administering the invention product indicates that the compositional ratio of the invention product is effective for amelioration of human bedsores.

In addition, the level of albumin, an important indicator for evaluation of nutrition, was 3.0 mg/dL with administration of the commercially available enteral nutritive product A but increased to 3.3 mg/dL after administration of the invention product, thus showing improvement in nutrition.

This demonstrated that the zinc and copper contents and ratio, the dosage of vitamin B complex (as an important factor for energy production) and the protein content in the invention product are effective for wound healing.

INDUSTRIAL APPLICABILITY

The total enteral nutritious composition of the invention exhibits an excellent effect for treatment or prevention of Protein Energy Malnutrition (PEM) in humans, and notable effects of improvement in serum level of albumin as an indicator of nutrition, amelioration of bedsores, improvement in albumin/globulin ratio, increase in reduced sodium and chloride content, improvement in hemoglobin, improvement in hematocrit, increase in serum zinc content and increase in peripheral lymphocyte count. Thus, the composition of the invention is useful for treatment or prevention of hypoalbuminemia and can be used for curing or prevention of bedsore or wounds. Moreover, since the composition of the invention has a high sodium content it is useful for treatment or prevention of hyponatremia. The composition of the invention also has a high zinc content and can therefore be used for treatment or prevention of patients with zinc deficiency. Finally, the composition of the invention can also be used to improve hemoglobin and hematocrit values and prevent their decrease.

What is claimed is:

1. A total enteral nutritious composition comprising proteins, sugars, fats, minerals and vitamins, wherein said total enteral nutritious composition comprises a copper content of 0.09 to 0.15 mg, a zinc content of 1.5 to 3.0 mg, a zinc/copper weight ratio of 10/1-25/1, a sodium content of 185 mg or greater, a vitamin B1 content of 0.30 mg or greater and a vitamin B2 content of 0.25 mg or greater, per 100 kcal of the composition.

2. A total enteral nutritious composition according to claim 1, wherein the protein content is 4.0 g or greater per 100 kcal of the composition.

3. A total enteral nutritious composition according to claim 2, wherein the protein content is 5.0 g or greater per 100 kcal of the composition.

4. A total enteral nutritious composition according to claim 1, wherein the zinc content is 1.5-3.0 mg, the copper content is 0.09 to 0.15 mg, the sodium content is 185-385 mg, the vitamin B1 content is 0.4-2.0 mg, the vitamin B2 content is 0.25-2.0 mg and the zinc/copper weight ratio is 10/1-20/1, per 100 kcal of the composition.

5. A total enteral nutritious composition according to claim 4, wherein the zinc/copper weight ratio is between 13/1 and 20/1.

6. A total enteral nutritious composition according to claim 5, wherein the zinc/copper weight ratio is between 15/1 and 18/1.

7. A total enteral nutritious composition according to claim 1, wherein the zinc content is 1.8-3.0 mg, the copper content is 0.09-0.12 mg and the sodium content is 200-385 mg, per 100 kcal of the composition.

8. A total enteral nutritious composition according to claim 1, wherein the vitamin B6 content is 0.3-2.0 mg and the biotin content is 1.0-10 µg, per 100 kcal of the composition.

9. A total enteral nutritious composition according to claim 1, wherein the vitamin B12 content is 0.20-0.70 µg, the folic acid content is 20-80 µg, the β-carotene content is 100-450 µg and the vitamin C content is 10-70 mg, per 100 kcal of the composition.

10. A total enteral nutritious composition according to claim 1, wherein the selenium content is 4.5-18 µg per 100 kcal of the composition.

11. A total enteral nutritious composition according to claim 1, wherein the proportion of animal protein to vegetable protein is between 4:1 and 1:4.

12. A total enteral nutritious composition according to claim 1, which contains as protein:
  (a) glutamine peptides, and
  (b) soybean protein or a soybean hydrolysate.

13. A total enteral nutritious composition according to claim 12, wherein the total glutamine in the protein is at least 0.6 g per 100 kcal of the composition.

14. A total enteral nutritious composition according to claim 13, wherein the proportion of glutamine peptide to soybean protein or its hydrolysate is between 4:1 and 1:4.

15. A total enteral nutritious composition according to claim 12, wherein the proportion of glutamine peptide to soybean protein or its hydrolysate is between 4:1 and 1:4.

16. A total enteral nutritious composition according to claim 1, which contains as fat sources medium-chain fatty acid oils in an amount of at least 35 wt % of the fat, wherein the ratio of ω-3 fatty acids to ω-6 fatty acids in the fat is between 1:10 and 1:1.

17. A total enteral nutritious composition according to claim 16, wherein the medium-chain fatty acid triglycerides constitute 40-65 wt % of the fat and the ratio of ω-3 fatty acids to ω-6 fatty acids in the fat is between 1:4 and 1:1.

18. A total enteral nutritious composition according to claim 1, wherein the viscosity of the composition is in the range of 6-18 mPa·s (25° C.).

* * * * *